United States Patent [19]

Curcio et al.

[11] Patent Number: 5,163,954
[45] Date of Patent: Nov. 17, 1992

[54] SUTURE RING FOR HEART VALVE PROSTHESES

[75] Inventors: Maria Curcio, Saluggia; Enrico Pasquino, Turin; Stefano Rinaldi, Parma; Franco Vallana, Turin, all of Italy

[73] Assignee: Sorin Biomedica SPA, Saluggia, Italy

[21] Appl. No.: 658,535

[22] Filed: Feb. 21, 1991

[30] Foreign Application Priority Data

Feb. 21, 1990 [IT] Italy .................. 67127 A/90

[51] Int. Cl.⁵ ............................... A61F 2/24
[52] U.S. Cl. ............................. 623/2; 623/900
[58] Field of Search .......................... 623/2, 900

[56] References Cited

U.S. PATENT DOCUMENTS

| | | | |
|---|---|---|---|
| 3,491,376 | 1/1970 | Shiley | 623/2 |
| 3,579,642 | 5/1971 | Hefferman et al. | 623/2 |
| 3,689,942 | 9/1972 | Rapp | 623/2 |
| 4,035,849 | 7/1977 | Angell et al. | 623/2 |
| 4,377,010 | 3/1983 | Fydelor et al. | 623/2 |
| 4,535,483 | 8/1985 | Klawitter et al. | 603/2 |

*Primary Examiner*—Stephen C. Pellegrino
*Assistant Examiner*—Gary Jackson
*Attorney, Agent, or Firm*—George P. Hoare, Jr.

[57] ABSTRACT

In a suture ring for heart valve prostheses, the internal surface of the ring which is intended to be exposed to the blood flow is covered by a substantially water-repellent material so that it absorbs substantially no blood and has little haemolytic effect. The outer surface of the ring which is intended to be exposed to the tissue to which the prosthesis is sutured is covered by a substantially hydrophilic, porous material so as to encourage the colonization of the ring by the tissue.

9 Claims, 1 Drawing Sheet

SUTURE RING FOR HEART VALVE PROSTHESES

FIELD OF THE INVENTION

The present invention relates to suture rings for heart valve prostheses and particularly concerns suture rings with internal surfaces which are intended to be exposed to the blood flow and external surfaces which are intended to be exposed to the tissue to which the prosthesis is sutured.

BACKGROUND OF THE INVENTION

Suture rings of the type specified above are widely known in the art.

These suture rings are usually covered (and, in some cases, constituted entirely) by fabrics made of biocompatible synthetic materials which are intended to form a woven structure through which surgical stitches can be inserted to suture the prosthesis in its implant position after the removal of the natural valve flaps.

Conflicting requirements must generally be taken into account in the selection of these materials.

On the one hand, it is desirable for the suture ring not to absorb blood or cause any appreciable resistance to the blood flow which might have a haemolytic or thrombogenic effect. This means that the selection of the covering material is oriented towards substantially water-repellent materials such as polytetrafluoroethylene (also known by the trade name of Teflon).

The use of these materials, however, conflicts with the need for the external region of the suture ring, which is exposed to the sutured tissue, to be colonized by that tissue so that, in time, the prosthesis becomes firmly anchored in its implant position.

This latter requirement could be satisfied very well with the use of substantially hydrophilic, porous materials such as, for example, polyethylene terephthalate (also known by the trade name of Dacron). These materials in turn are somewhat prone to absorbing blood and may also have a considerable haemolytic effect on the mass of blood to which the suture ring is exposed during use.

The object of the present invention is to provide a suture ring for heart valve prostheses in which the aforesaid requirements can be satisfied simultaneously without giving rise to the problems described.

SUMMARY OF THE INVENTION

According to the present invention, this object is achieved by virtue of a suture ring having the characteristics recited specifically in the claims.

The suture ring for a heart valve prosthesis has a first surface which is exposed to the blood flow and a second surface which is exposed to the tissue. The first and second surfaces have respective coverings of a first material and a second material which differ from each other.

The first material which covers the first surface is a substantially haemocompatible material which absorbs substantially no blood and has little haemolytic and thrombogenic effect. The second material covering the second surface is a substantially hydrophilic, porous material which encourages the colonization of the ring by some of the tissue.

Figure 1:
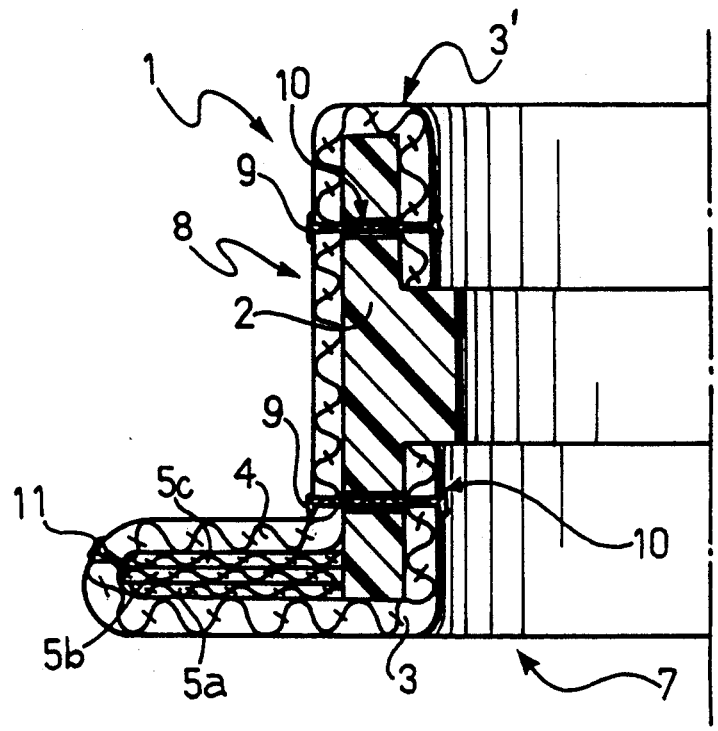
FIG. 1 is a partial section of a suture ring for a mitral valve prosthesis formed according to the invention.

In the drawings, a suture ring for heart valve prostheses is generally indicated by numeral 1.

In general terms and according to widely known principles, the ring in question is constituted substantially by a more or less flexible and resilient annular body which is intended to be fitted around the stent or housing of the valve prosthesis, not shown in the drawings, which supports the obturator means of the valve (pivoting obturators, etc.).

The function of the suture ring is essentially to provide for and to stimulate the firm anchorage of the prosthesis in its implant position. The prosthesis in question may either be of the mechanical type with pivoting obturators or of the type with natural valve flaps.

In general terms, the suture ring 1 can be seen to include:

a core 2 of rigid or semirigid material (for example, a paraformaldehyde polymer also known by the trade name of Delrin) preferably formed according to the criteria which are the subject of a parallel patent application filed on even date by the present Applicant (U.S. Ser. No. 658,555), and an outer covering layer constituted essentially by a fabric of biocompatible synthetic yarn; in the solution according to the invention, this outer covering is constituted by several layers or sheets of different by numerals fabrics, indicated 3 and 4, whose characteristics will be described further below.

In the suture ring of FIG. 1, which is intended to be fitted to a mitral valve prosthesis, an external loop is formed in the covering layer 3, 4 at one axial end of the core 2 and contains an annular mass of generally soft padding formed by several, for example, three, superposed layers 5a, 5b and 5c whose characteristics will be described further below.

Figure 2:
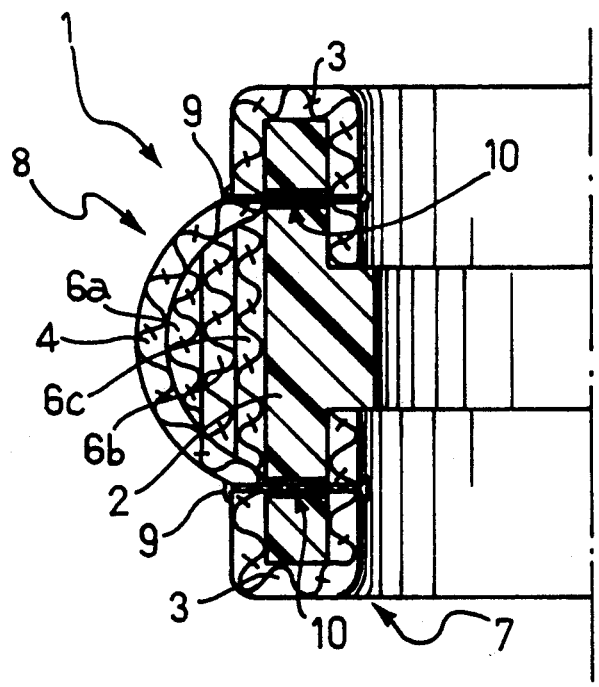
FIG. 2 is also a partial section showing the structure of a suture ring for an aortic valve prosthesis formed according to the present invention.

In the suture ring of FIG. 2, which is intended to be fitted to an aortic valve prosthesis, a loop is formed in the covering layer 3, 4 approximately in the middle of the external surface of the core 2; this loop also contains a mass of soft padding having a structure with several, for example, three, layers 6a, 6b and 6c.

According to widely known criteria which do not need to be repeated herein, surgical stitches are intended to extend through the external loops of the suture rings and their padding to keep the suture ring (and hence the prosthesis) securely in its desired implant position.

The main characteristic of the suture ring according to the invention is the selection of different materials for covering the surface 7 over which the blood passing through the axial orifice in the prosthesis is intended to flow when the prosthesis is in use, and for covering the surface 8 which is intended to be exposed to the tissue to which the prosthesis is sutured.

In the solution according to the invention, the surface 7 is covered by a material 3 which is preferably constituted by a fabric of a substantially water-repellent synthetic material so that it absorbs substantially no blood and has little haemolytic effect.

According to a solution currently preferred by the Applicant, the material 3 is constituted by a polytetrafluoroethylene (Teflon) fabric, preferably of the type currently known in the art as "light Teflon".

In the suture ring of FIG. 1 (the mitral prosthesis), the water-repellent material 3 extends mainly along the edge of the core 2 of the ring and along the side of the suture loop at the end of the ring which is intended to be oriented upstream with respect to the blood flow through the prosthesis (the so-called "inflow" end); in other words, this is the end of the prosthesis over which the blood is intended to flow in use.

The second covering layer 4 of hydrophilic, porous material, however, extends from the opposite side of the suture loop over the entire outer surface of the core 2 and forms a turned-back portion 3' facing the internal surface of the core 2 of the suture ring.

The covering layer 4 is preferably made of polyethylene terephthalate (Dacron) with a velvety structure of the type currently known in the art as "double velour".

This is a fabric whose structure is such as to encourage the colonization of the suture ring by some of the tissue surrounding it.

Both the covering layer 3 and the turned-back portion 3' are coated with a biocompatible carbon material preferably produced according to the criteria described in European patent applications Nos. 0 102 328 and 0 224 080, both in the name of the present Applicant.

This coating improves the biocompatibility of the material to which it is applied and also modifies its behavior to a certain extent as regards its haemocompatibility characteristics.

This applies mainly to the internal turned-back portion 3' which (although its basic structure is made of the hydrophilic material of the layer 4) behaves in a substantially haemocompatible manner like the material 3 since it is covered by biocompatible carbon.

The wording adopted in the claims which follow, according to which the first and second covering materials differ from each other, is therefore intended to mean that the two materials in question behave differently with respect to the mass of blood and to body tissue. This different behavior may result either from the different chemical natures of their basic constituents or, as in the case of the turned-back portion 3', from a particular treatment which modifies the behavior of the basic material.

As regards the structure of the mass of padding 5a–5c of the external loop of the suture ring of FIG. 1, the Applicant has found that the use of a material substantially similar to that used for the outer covering layer 4 (that is, polyethylene terephthalate) is particularly advantageous for the first layer 5a behind the first covering layer 3. Without wishing to be bound by any specific theory in this connection, he has reason to believe that the presence of the polyethylene terephthalate of the layer 5a contributes to the formation and firm retention of a proteinaceous layer on the outer covering layer 3 during the period after the implantation of the prosthesis. The presence of this proteinaceous layer has been found to be particularly beneficial in minimizing the chance of the prosthesis giving rise to thromboembolic complications.

The use of a felt of polytetraflurorethylene (that is, the material of the inner covering layer 3) has been found particularly to be advantageous for forming the intermediate layer 5b of the padding since it has good characteristics of consistency and softness and can be penetrated easily by the surgical needles used for implanting the prosthesis. For the remaining layer 5c, it is thought preferable again to use a material just like that of the outer covering layer 4 so as further to improve its functional characteristics.

The covering layer 3, 4, 3' is sewn to the core (according to generally known criteria) by stitches 9 extending through radial holes 10 in the core 2.

The two covering layers 3, 4 are connected together (also by stitches 11) in a circle approximately on the outer edge of the suture loop.

The foregoing also applies substantially to the suture ring for aortic prostheses of FIG. 2, except for the different arrangement of the suture loop.

In this case, the water-repellent layer 3 is divided into two portions which cover the opposite ends of the core 2 and extend over most of its internal surface, leaving only a central tab-like appendage of the core 2 free (as in the ring of FIG. 1). The characteristics and function, of this appendage are described in U.S. Ser. No. 658,555 filed by the Applicant on even date and already referred to above.

Both parts of the covering layer 3 of the ring of FIG. 2 are coated with biocompatible material according to the European patent applications Nos. 0 102 328 and 0 224 080 already cited above.

As regards the outer mass of padding, the sequence of layers 5a–5c given above is repeated for the layers 6a–6c.

The outermost layer 6a is thus made of a hydrophilic, porous material (Dacron) which improves the characteristics of the outer layer 4 that encourage the colonization of the suture ring by the surrounding tissue. The intermediate layer 6b is made of polytetrafluoroethylene felt which is bulky and can be penetrated easily by surgical needles. The innermost layer 6c is made of a material identical to that outer layer 6a. In this embodiment also, the covering layer is anchored to the core 2 by stitching 9 through the apertures 10 in the core 2.

The padding of the suture loop may, however, have a layered structure including a different number of layers (for example, only two layers, the innermost layer 6c in the prosthesis of FIG. 2 being omitted).

Naturally, the principle of the invention remaining the same, the details of construction and forms of embodiment may be varied widely with respect to those described and illustrated, without thereby departing from the scope of the present invention.

What is claimed is:

1. A suture ring for heart valve prostheses, comprising a first surface which is exposed to the blood flow and a second surface which is exposed to the tissue to which the prosthesis is sutured, wherein:
   the first and second surfaces have respective coverings of a first material and a second material which differ from each other,
   the first material covering the first surface is a substantially haemocompatible material so that it absorbs substantially no blood and has little haemolytic and thrombogenic effect, and
   the second material covering the second surface is a substantially hydrophilic, porous material which encourages the colonization of the ring by some of the tissue.

2. A suture ring according to claim 1, wherein at least part of one of the said materials is made of a basic constituent identical to the basic component of the other of the said materials, and at least the said part is treated to make it substantially similar to the said one of the materials.

3. A suture ring according to claim 1, wherein the first and second materials are woven materials.

4. A suture ring according to claim 1, wherein the first material is polytetrafluoroethylene.

5. A suture ring according to claim 1, wherein the first material has a surface coating of a biocompatible carbon material.

6. A suture ring according to claim 1, wherein the second material is polyethylene terephthalate.

7. A suture ring according to claim 1, wherein the second material has a velvety appearance.

8. A suture ring for a heart valve prothesis, comprising a first surface which is exposed to the blood flow and a second surface which is exposed to the tissue to which the prosthesis is sutured, wherein:
  (a) the first and second surfaces have respective coverings of a first material and a second material which differ form each other;
  (b) the first material covering the first surface comprises a substantially haemocompatible material which absorbs substantially no blood and has little haemolytic and thrombogenic effect;
  (c) the second material covering the second surface comprises a substantially hydrophilic, porous material which encourages the colonization of the ring by some of the tissue; and
  (d) an external suture loop with a layered mass of padding in a generally sandwich-like configuration with an inner layer of a material substantially like the first material and at least one outer layer of a material substantially like the second material.

9. A suture ring according to claim 8, wherein the external loop further comprises an end surface over which the blood flows, wherein the end surface is covered by the first material and the mass of padding includes a layer of a material substantially like the second material behind the end surface which is covered by the first material.

* * * * *